(12) United States Patent
Chen et al.

(10) Patent No.: US 9,861,808 B2
(45) Date of Patent: Jan. 9, 2018

(54) CONDUCTIVE MULTI-LAYER POLYMER CATHETER FOR ACTIVE IMPLANTABLE MEDICAL DEVICE LEADS AND EXTENSIONS

(71) Applicant: MRISafetyModeling, LLC, Sugar Land, TX (US)

(72) Inventors: Ji Chen, Sugar Land, TX (US); Francois Alesch, Vienna (AT)

(73) Assignee: MRIsafetymodeling, LLC, Sugar Land, TX (US)

( * ) Notice: Subject to any disclaimer, the term of this patent is extended or adjusted under 35 U.S.C. 154(b) by 0 days.

(21) Appl. No.: 14/875,380

(22) Filed: Oct. 5, 2015

(65) Prior Publication Data

US 2016/0296744 A1 Oct. 13, 2016

Related U.S. Application Data

(63) Continuation of application No. PCT/US2015/052989, filed on Sep. 29, 2015.

(60) Provisional application No. 62/144,206, filed on Apr. 7, 2015.

(51) Int. Cl.
| | | |
|---|---|---|
| *A61N 1/00* | (2006.01) | |
| *A61N 1/05* | (2006.01) | |
| *A61L 29/04* | (2006.01) | |
| *A61L 29/08* | (2006.01) | |
| *A61L 29/14* | (2006.01) | |
| *G01R 33/28* | (2006.01) | |

(Continued)

(52) U.S. Cl.
CPC ............... *A61N 1/05* (2013.01); *A61L 29/04* (2013.01); *A61L 29/085* (2013.01); *A61L 29/14* (2013.01); *A61N 1/086* (2017.08); *G01R 33/288* (2013.01); *G01R 33/3685* (2013.01)

(58) Field of Classification Search
CPC ........ A61L 29/14; A61L 29/085; A61L 29/04; A61M 25/0045; A61N 1/05; A61N 1/086; G01R 33/288; G01R 33/3685
See application file for complete search history.

(56) References Cited

U.S. PATENT DOCUMENTS

| | | | |
|---|---|---|---|
| 6,508,806 B1 * | 1/2003 | Hoste | A61M 25/0012 138/124 |
| 8,343,212 B2 | 1/2013 | Pickett et al. | |
| 8,380,306 B2 | 2/2013 | Pickett | |

(Continued)

OTHER PUBLICATIONS

Kant, Ankur; Design and Patterning of Polypyrrole Interconnects for Cochlear Implant, in the Department of Chemical & materials Engineering of the College of Engineering in the Division of Research and Advanced Studies of the University of Cincinnati, Feb. 3, 2006.

(Continued)

*Primary Examiner* — George Manuel
(74) *Attorney, Agent, or Firm* — Weisun Rao; Jonathan Giroux; Greenberg Traurig, LLP (57) ABSTRACT

An active implantable medical device (AIMD) lead implanted into a patient's body may include at least one conductive filer electrically coupled to a distal electrode and a polymer jacket for insulating the conductive filer. A conductive multi-layer polymer catheter may be disposed around an outside of the insulating polymer jacket to reduce, or entirely eliminate, the conductive filer's exposure to electromagnetic radiation.

1 Claim, 5 Drawing Sheets

(51) Int. Cl.
  *G01R 33/36* (2006.01)
  *A61N 1/08* (2006.01)

(56) References Cited

U.S. PATENT DOCUMENTS

| | | |
|---|---|---|
| 8,577,476 B2 | 11/2013 | Hendricks et al. |
| 8,805,536 B2 * | 8/2014 | Li .......................... H01R 43/16 607/116 |
| 2005/0222658 A1 | 10/2005 | Hoegh |
| 2008/0033497 A1 | 2/2008 | Bulkes |
| 2011/0257504 A1 | 10/2011 | Hendricks et al. |
| 2011/0301677 A1 | 12/2011 | Hendricks et al. |
| 2012/0029585 A1 | 2/2012 | Pickett |
| 2012/0330383 A1 | 12/2012 | Wahlstrand |
| 2014/0058489 A1 | 2/2014 | Hendricks et al. |
| 2014/0277318 A1 | 9/2014 | Richardson-Burns et al. |

OTHER PUBLICATIONS

Ateh, D. D.; "Polypyrrole-based Conducting Polymers and Interactions with Biological Tissues," Journal of the Royal Society Interface, Jun. 22, 2006; 2006.0141, 741-52; Royal Society Publishing.

* cited by examiner

CONDUCTIVE MULTI-LAYER POLYMER CATHETER FOR ACTIVE IMPLANTABLE MEDICAL DEVICE LEADS AND EXTENSIONS

CROSS REFERENCE TO RELATED APPLICATIONS

This application claims priority to U.S. application Ser. No. 62/144,206, filed on Apr. 7, 2015 and International Application No. PCT/US2015/052989, filed on Sep. 29, 2015, the contents of which are incorporated herein by reference in their entireties.

FIELD OF THE INVENTION

The present disclosure relates generally to active implantable medical devices (AIMDs) and, more particularly, to the leads and extensions for use in conjunction with an AIMD.

BACKGROUND OF THE INVENTION

Active implantable medical devices (AIMDs) are commonly used to apply electrical pulses to various parts of the human body, such as the heart of a patient with a cardiovascular condition. As further examples, AIMDs may comprise cardiac pacemakers and defibrillators, spinal cord stimulators (SCS) for pain therapy, dorsal root ganglion stimulators (DRG stimulators), motor cortex stimulators, diaphragm stimulators, cochlear implants, and deep brain stimulators (DBS) for epilepsy therapy. Other examples of AIMDs include gastric nerve stimulators, bladder stimulators, and stimulators for peripheral or cranial nerves [e.g., for the treatment of migraine respectively sleep apnea (hypoglossal) and epilepsy (vagal)]. AIMDs can even be used to administer drugs, to monitor vitals, to minimize the effects of movement disorders, or to monitor or minimize psychiatric conditions. Those having ordinary skill in the art will appreciate that the above list of devices and applications for AIMDs is not in any way exhaustive. Indeed, new applications for AIMDs are constantly reported and evolving.

A typical AIMD includes an active part, such as a metal can containing electrical circuits that generate therapeutic electric pulses; a power supply, such as a primary cell or a rechargeable battery; and a one- or two-way radio that allows the AIMD to communicate with components that are not implanted, such as a programming device, for example. Many AIMDs also include a conducting component, a lead, and an extension. The active part is usually coupled to the lead, which along with the extension delivers the therapeutic pulses to a recipient body part such as a heart, a brain, a spinal cord, or nerves. It is common for the active part to be implanted at sites that are relatively comfortable for the patient. For instance, active parts are typically implanted in a pectoral (i.e., the chest), an infracostal, or a gluteal area. The lead may be connected either directly to the active part or, in some cases where longer distances have to be bridged, by way of an extension that is used to connect the lead and the active part. The total length of a lead an extension can in many cases exceed 100 cm. Such a length does not affect the quality of the stimulation and do not overcomplicate the surgical procedure, as these components are well tolerated by the subcutaneous tissue where these components are positioned using special tunneling devices. Extensions that are too short can cause unwanted mechanical stress, which in some cases can result in wire fractures. For this reason, surgeons prefer a slight surplus in terms of length, as the surgeons can kink and/or coil the excess lead or extension. Moreover, tunneling is a routine procedure that is simple and safe. However, those having ordinary skill in the art will understand that tunneling can be a delicate task when performed in certain locations, such as the neck, where crossing vessels can lead to hematomas.

However, one of the major problems of using a lengthy conducting material that passes through subcutaneous tissue (i.e., the AIMD lead and its extensions) is that the lengthy conducting material acts as an antenna. As a result, the lengthy conducting material can become problematic when a patient is exposed to an electromagnetic field that interacts with the lengthy conducting material. Many patients having AIMDs must avoid strong electromagnetic fields created by common devices such as metal detectors, article surveillance security systems, airport scanners, cell phones, and wireless communication devices, to name a few. Electromagnetic fields are also used in one the most important medical imaging technologies, namely, Magnetic Resonance Imaging (MRI). Thus, patients with AIMDs are typically not allowed to access MRI scanners, which are very important diagnostic tools.

Therefore, a need exists for a device that prevents, or at least substantially reduces, the effects of electromagnetic fields on AIMDs.

SUMMARY OF THE INVENTION

In one aspect, the present invention provides a conductive multi-layer polymer catheter to be disposed around and outside an active implantable medical device, wherein the active implantable medical device comprises a lead having at least one conductive filer electrically coupled to a distal electrode and surrounded by at least one insulating jacket, the conductive multi-layer polymer catheter comprises an outer conductive polymer layer positioned outside the at least one insulating jacket and configured to contact a body tissue of a patient once implanted.

In some embodiments, the multi-layer polymer catheter further includes an inner conductive polymer layer or an insulating polymer layer, wherein the inner conductive polymer layer is positioned around and outside the at least one insulating jacket but within (and inside) the outer conductive polymer layer; the insulating polymer layer is positioned around and outside the insulating jacket and inside the outer conductive polymer layer (and also the inner conductive polymer layer if existing).

In some other embodiments, the multi-layer polymer catheter further includes an inner conductive polymer layer and an insulating polymer layer, wherein the inner conductive polymer layer is positioned around and outside the at least one insulating jacket but within (and inside) the outer conductive polymer layer; and the insulating polymer layer is positioned around and outside the insulating jacket and outer conductive polymer layer (and also within or inside the inner conductive polymer layer). As such, the multi-layer polymer catheter would comprise, from conductive filer out, the insulating jacket, inner conductive polymer layer, insulating polymer layer, and the outside conductive polymer layer.

In some embodiments, the conductive multi-layer polymer catheter comprising an inner conductive polymer layer that can be positioned around and outside the at least one insulating jacket; an insulating polymer layer positioned around and outside the inner conductive polymer layer; and an outer conductive polymer layer positioned around and outside the insulating polymer and configured to contact a body tissue of a patient once implanted, wherein the inner conductive polymer layer, the insulating polymer layer, and the outer conductive polymer layer cooperate to distribute electromagnetic radiation from external sources along at least a portion of a length of the lead of the active implantable medical device.

In some other embodiments, the conductive multi-layer polymer catheter further comprises one or more conductive polymer layers or one or more insulating polymer layers between the inner conductive polymer layer and outer conductive polymer layer.

In still some other embodiments, the insulating polymer layer comprises polyurethane, silicone, epoxy, poly ether ether ketone, acrylic, cyanoacrylate, epoxides, polyester, vinyl ester, a derivative, copolymer, or homopolymer thereof.

In still some other embodiments, each of the one or more conductive polymer layers comprises polypyrrole, polythiophene, polyethylenedioxythiophene, polyaniline, polyacetylene, a natural or synthetic melanin, a derivative, copolymer, or homopolymer thereof.

In still some other embodiments, the inner conductive polymer layer comprises a continuous conductive surface that extends along a length of the at least one insulating jacket.

In still some other embodiments, the conductive multi-layer polymer catheter further comprises a thermoset polymer that is in contact with a portion of the lead or an extension of the lead.

In still some other embodiments, the inner conductive polymer layer, the insulating polymer layer, and the outer conductive polymer layer of the conductive multi-layer polymer catheter are lengthwise slotted such that the conductive multi-layer polymer catheter can be retrofitted in-situ to the lead of an active implantable medical device or its extension.

In general, the conductivity and permittivity of one or more conductive layer of the conductive multi-layer polymer catheter is modified to maximize the shielding effect of the conductive multi-layer polymer catheter on the active implantable medical device, and the modification depends on the intended application, e.g., AIMD type, lead and extension type and material, and location of the AIMD in the body.

In another aspect, the present invention provides a conductive multi-layer polymer catheter tube which comprises:
   an optional inner conductive polymer layer that can be positioned around and outside an insulating jacket of an active implantable medical device;
   an optional insulating polymer layer positioned around the inner conductive polymer layer; and
   an outer conductive polymer layer positioned around the insulating polymer, the outer conductive polymer layer configured to contact a body tissue of a patient once implanted, wherein the optional inner conductive polymer layer, the insulating polymer layer, and the outer conductive polymer layer operate to distribute electromagnetic radiation from external sources along at least a portion of a length of a lead of the active implantable medical device.

In some embodiments, the conductive multi-layer polymer catheter tube comprises an inner conductive polymer layer that can be positioned around and outside an insulating jacket of an active implantable medical device; an insulating polymer layer positioned around the inner conductive polymer layer; and an outer conductive polymer layer positioned around the insulating polymer, the outer conductive polymer layer configured to contact a body tissue of a patient once implanted.

In some embodiments, the conductive multi-layer polymer catheter tube further comprises one or more supplemental conductive polymer layers and/or one or more supplemental insulating polymer layers between the inner conductive polymer layer and the outer conductive polymer layer.

In some embodiments, each of the one or more insulating polymer layers comprises polyurethane, silicone, epoxy, poly ether ether ketone, acrylic, cyanoacrylate, epoxides, polyester, vinyl ester, a derivative, copolymer, or homopolymer thereof.

In some embodiments, each of the one or more conductive polymer layers comprises polypyrrole, polythiophene, polyethylenedioxythiophene, polyaniline, polyacetylene, a natural or synthetic melanin, a derivative, copolymer, or homopolymer thereof. The conductivity and permittivity of one or more conductive layer can be modified to maximize the shielding effect of the conductive multi-layer polymer catheter on the active implantable medical device.

A third aspect of the present invention provides an active implantable medical device, comprising:
   a lead having a length and at least one conductive filer electrically coupled to a distal electrode,
   at least one insulating jacket surrounding the at least one conductive filer;
   a conductive multi-layer polymer catheter comprising an optional inner conductive polymer layer that can be positioned around and outside the at least one insulating jacket, an optional insulating polymer layer positioned around and outside the inner conductive polymer layer, and an outer conductive polymer layer positioned around and outside the insulating polymer, and configured to contact a body tissue of a patient once implanted, wherein the conductive multi-layer polymer catheter distributes electromagnetic radiation from external sources along at least a portion of the length of the lead.

In some embodiments, the conductive multi-layer polymer catheter comprises an inner conductive polymer layer that can be positioned around and outside the at least one insulating jacket, an insulating polymer layer positioned around and outside the inner conductive polymer layer, and an outer conductive polymer layer positioned around and outside the insulating polymer, and configured to contact a body tissue of a patient once implanted.

In some other embodiments, the conductive multi-layer polymer catheter further comprises one or more conductive polymer layers or one or more insulating polymer layers between the inner conductive polymer layer and the outer conductive polymer layer.

In some other embodiments of the active implantable medical device, the insulating polymer layer comprises polyurethane, silicone, epoxy, poly ether ether ketone, acrylic, cyanoacrylate, epoxides, polyester, vinyl ester, a derivative, copolymer, or homopolymer thereof.

In still some other embodiments of the active implantable medical device, each of the one or more conductive polymer layers comprises polypyrrole, polythiophene, polyethylenedioxythiophene, polyaniline, polyacetylene, a natural or synthetic melanin, a derivative, copolymer, or homopolymer thereof. The conductivity and permittivity of one or more conductive layer of the conductive multi-layer polymer catheter is modified to maximize the shielding effect of the conductive multi-layer polymer catheter on the active implantable medical device, and the modification depends on the intended application, e.g., AIMD type, lead and extension type and material, and location of the AIMD in the body.

In one example, a conductive multi-layer polymer catheter may comprise alternating layers of conductive polymers and insulating polymers disposed around an AIMD lead and extensions of the AIMD lead. In some examples, the conductive multi-layer polymer catheter may be assembled with the AIMD. In other examples, however, the conductive multi-layer polymer catheter may be assembled separately so as to form a multi-layer polymer tube. In those examples, the tube may be placed over the AIMD leads or the extensions of the AIMD before the initial implantation of the AIMD or to retrofit existing leads of AIMDs. Furthermore, those having ordinary skill in the art will understand that the number of conductive and insulating polymeric layers in the conductive multi-layer polymer catheter or tube may vary from one application to another.

Further, the conductive multi-layer polymer catheter may reduce or entirely eliminate an antenna effect associated with the leads and lead extensions of the AIMDs from electromagnetic radiation. As a result, the conductive multi-layer polymer catheter thereby protects the implanted AIMD leads and lead extensions from electromagnetic fields. In particular, the conductive multi-layer polymer catheter may protect the AIMD leads and lead extensions by distributing electromagnetic radiation along at least a portion of a length of an insulating layer surrounding one or more conductive filers of the AIMD lead. Nevertheless, the conductive multi-layer polymer catheter may be employed with a wide variety of AIMDs to minimize or even eliminate unwanted interaction between the AIMD leads and its extensions and electromagnetic fields.

BRIEF DESCRIPTION OF THE DRAWINGS

The figures described herein are for illustrative purposes only and are not meant to depict all possible implementations. Likewise, the figures in no way limit the scope of the present disclosure. For further understanding of the nature and objects of this disclosure, reference should be made to the following description, taken in conjunction with the accompanying drawings in which like parts are given like reference materials.

DETAILED DESCRIPTION OF THE INVENTION

The following description of exemplary apparatus is intended to be illustrative of the present invention, but not intended to limit the scope of the enclosed claims to a precise form or forms detailed herein.

Figure 1:
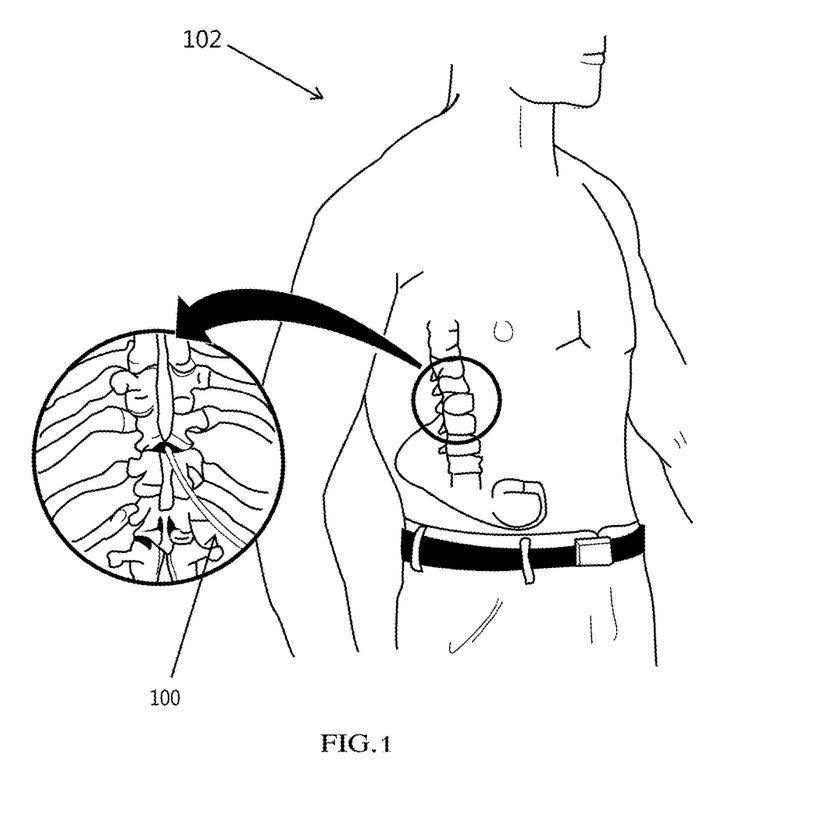
FIG. 1 illustrates an example AIMD system implanted in a patient.
Figure 2:
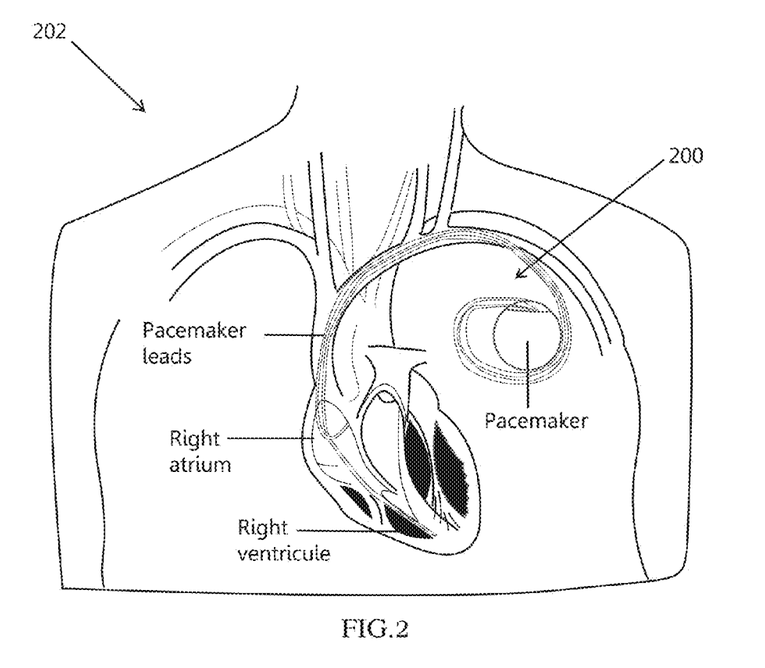
FIG. 2 illustrates an example pacemaker system implanted in a patient.

As explained above, a lead of an AIMD or an extension of the lead may have one or more conductive filers coupled to at least one distal electrode. The AIMD lead may have at least one conductive filer electrically coupled to the distal electrode as well as a polymer jacket or other insulating layer that insulates the conductive filer. FIG. 1 illustrates an example AIMD system 100 implanted in a patient 102. Likewise, FIG. 2 illustrates a more specific type of AIMD system, i.e., a pacemaker 200, implanted in a patient 202.

A conductive multi-layer polymer catheter may be disposed around the insulating polymer jacket. In some examples, the conductive multi-layer polymer catheter may comprise a continuous conductive surface that extends along a length of an external surface of the insulating polymer jacket of the AIMD lead and its extension. The conductive part of the multi-layer polymer catheter can be in contact with a portion of the lead or its extension or in contact with the surrounding tissue. If the conductive part of the multi-layer polymer catheter is in direct contact with the surrounding tissue, the impact of electromagnetic radiation on the conductive filer may be substantially reduced or even eliminated, possibly due to dissipation of the electromagnetic power along the surface of the polymer catheter. Electromagnetic radiation may be caused by a multitude of sources and may take a multitude of forms such as, for example, a radio frequency (RF) field. Moreover, one example way in which the conductive multi-layer catheter may reduce the impact of electromagnetic radiation on the conductive filer is by distributing absorbed electromagnetic radiation along a substantial portion, or even an entire length, of the lead or its extension. One or more conductive layers outside the conductive lead or the extension cause electromagnetic radiation to travel longitudinally along a length of the one or more conductive layers, as opposed to traveling primarily radially inwards towards the lead or the extension. The act of distributing the effects of external electromagnetic fields across the length of one or more conductive layers, the lead, and/or the extension considerably improves the safety of the AIMD.

In some examples, the conductive multi-layer catheter may comprise a single conductive polymer layer disposed around the AIMD leads and extensions. In other examples, however, the conductive multi-layer polymer catheter may comprise a plurality of conductive polymer layers. For instance, 2-25, 5-15, or 7-15, 8-12, 9, 10, or 11 layers of same or different conductive polymer(s) can be included in a catheter of this invention. Each of the single or plural conductive polymer layers can have a thickness of, e.g., 0.1-10.0 micrometer, 0.2-7.5 micrometer, 0.2-5.0 micrometer, 0.2-2.5 micrometer, 0.2-1.0 micrometer, 0.25 micrometer, or 0.5 micrometer. Further, in some cases, two or more of the conductive polymer layers may be separated by at least one insulating polymer layer between the conductive polymer layers. Each of the insulating polymer layers may comprise one or more of the following example insulating materials: polyurethane, silicone, epoxy, PEEK (i.e., poly ether ketone), acrylic, cyanoacrylate, epoxides, polyester, and vinyl ester. On the other hand, each of the conductive polymer layers may comprise one or more of the following example conducting materials: polypyrrole, polythiophene, polyethylenedioxythiophene (i.e., PEDOT), polyaniline, polyacetylene, natural or synthetic melanins, or a derivative, copolymer or homopolymer thereof. The composition, conductivity, and permittivity of each of the polymer layer(s) can be adjusted to achieve maximum shielding of the electromagnetic energy.

One of ordinary skill in the art would understand that the conductive polymer layers and the insulating polymer layers may be formed in a variety of ways. In one example, for instance, conductive polymer layers may be coated or deposited onto an outer and/or inner surface of an insulating polymer layer. Further, at least in some examples, an innermost layer and an outermost layer of the conductive multi-layer catheter may comprise conductive materials (e.g., a conductive polymer or a metal salt). The outermost layer of the catheter, or at least a substantial portion of the outermost layer of the catheter, may in many cases be in electrical contact with surrounding tissue. In many examples there is no other layer positioned around and outside the outer conductive polymer layer. Such an arrangement helps dissipate electromagnetic energy. Further, the innermost layer of the conductive multi-layer catheter may be in electrical contact with the outer surface of the AIMD lead or its extension and in contact with the body fluids between the outer surface of the AIMD lead or its extension and the inner layer of the conductive multi-layer polymer catheter.

Furthermore, the conductive multi-layer polymer catheter reduces and, in some cases, entirely prevents the conductive filer from acting as an antenna for RF waves and other types of electromagnetic radiation. In other words, the conductive multi-layer polymer catheter creates a local shield that protects the implanted AIMD leads and extensions from electromagnetic fields. It should be understood that the conductive multi-layer catheter may be applied to a wide variety of AIMDs to reduce and/or prevent interactions between the leads and their extensions and electromagnetic fields.

Figure 3:
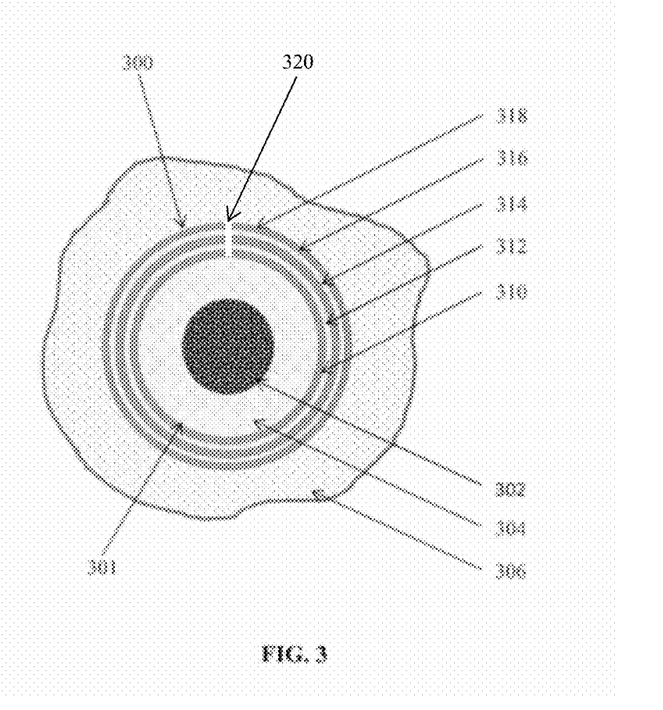
FIG. 3 is cross-sectional view of an example multi-layer polymer catheter surrounding an example AIMD lead and example extensions.

FIG. 3 shows a cross-sectional view of an example conductive multi-layer polymer catheter 300 deposited on top of an AIMD lead 301. The AIMD lead 301 in this example comprises one or more conductive filers 302 and an insulating polymer jacket 304 for housing the conductive filers 302. The AIMD lead 301 and the example conductive multi-layer polymer catheter 300 are represented as having been implanted within a patient's body, as the example conductive multi-layer polymer catheter 300 is shown to be in contact with tissue 306.

The example conductive multi-layer polymer catheter 300 may comprise an inner conductive polymer layer 310, which may be disposed around the insulating jacket 304 of the AIMD lead 301. In this example, an insulating polymer layer 312 may be disposed around the inner conductive polymer layer 310. Further, a conductive polymer middle layer 314 may be disposed around the insulating polymer layer 312. Another insulating polymer layer 316 may be disposed around the conductive polymer middle layer 314, and an outer conductive polymer layer 318 may be disposed around the insulating polymer layer 316. Thus, the example conductive multi-layer polymer catheter 300 shown in FIG. 3 comprises the inner conductive polymer layer 310, the insulating polymer layer 312, the conductive polymer middle layer 314, the insulating polymer layer 316, and the outer conductive polymer layer 318, where the outer conductive polymer layer 318 is in contact with the body tissue 306. In most examples, the outermost layer of the example conductive multi-layer polymer catheters disclosed herein is a conductive polymer layer, not an insulating polymer layer. And as a general matter, the conductive polymer layers 310, 314, 318 are not conductive filers and do not carry electric signals to or from distal electrodes. Further, as also shown in FIG. 3, the layers 310, 312, 314, 316, 318 of the example conductive multi-layer polymer catheter 300 may in some examples be separate, separable, and/or distinct from one another and may not have been formed together.

Those having ordinary skill in the art will understand that in some examples the conductive multi-layer polymer catheter 300 may be assembled while it is being secured to the AIMD lead 301. In other examples, though, the conductive multi-layer polymer catheter 300 may be assembled separately from the AIMD lead 301 and disposed about the AIMD lead 301 when convenient. Likewise, those having ordinary skill in the art will also understand that the example conductive multi-layer polymer catheter 300 shown in FIG. 3 is merely illustrative. For instance, in other examples a conductive multi-layer polymer catheter may include three layers or seven layers instead. Still further, the example conductive multi-layer polymer catheters disclosed herein may come in different sizes, shapes, and forms. As an example, the conductive multi-layer polymer catheter may be a solid tube, with an inner lumen wide enough to be put over the AIMD lead and its extensions before the initial implantation. The conductive multi-layer polymer catheter may also be slotted lengthwise (see slot 320) to be put, in situ, over existing AIMD leads and extensions.

Figure 4:
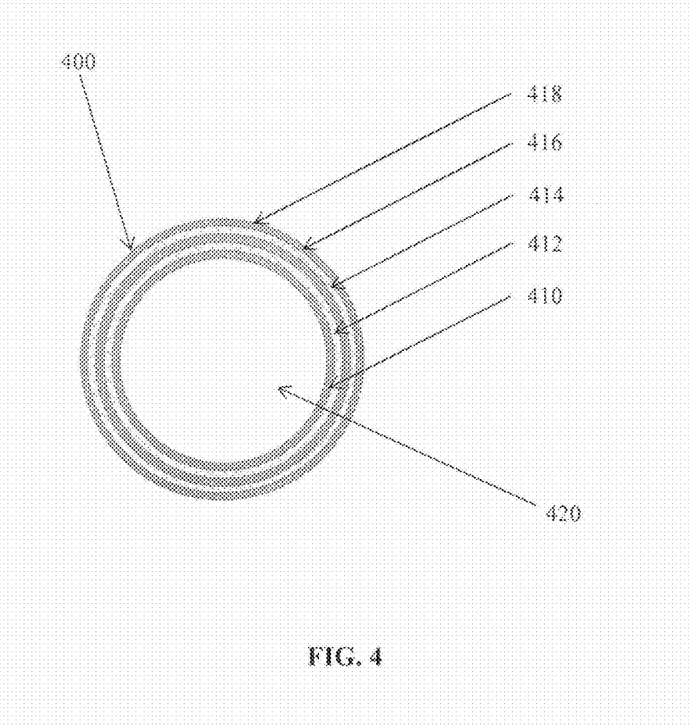
FIG. 4 is cross sectional view of an example multi-layer polymer catheter tube.

FIG. 4 illustrates an example conductive multi-layer polymer catheter tube 400. Similar to the example conductive multi-layer polymer catheter 300 illustrated in FIG. 3, the conductive multi-layer polymer catheter tube 400 may comprise an inner conductive polymer layer 410, an insulating polymer layer 412, a conductive polymer middle layer 414, a second insulating polymer layer 416, and an outer conductive polymer layer 418. An inner lumen 420 may extend through an inside of the conductive multi-layer polymer catheter tube 400. While the example conductive multi-layer polymer catheter tube 400 of FIG. 4 comprises three conductive polymer layers, the number of conductive polymer layers may be modified as explained above. The conductive multi-layer polymer catheter tube 400 of FIG. 4 may also include one or more features as disclosed with respect to the various layers shown in FIG. 3.

In some instances, the conductive multi-layer polymer catheter tube 400 may be implanted within a body before the AIMD and the lead 301 are implanted. However, once implanted, the conductive multi-layer polymer catheter tube 400 creates a subcutaneous tunnel. As such, the conductive multi-layer polymer catheter tube 400 may act as a guide when the AIMD is inserted. Moreover, the conductive multi-layer polymer catheter tube 400 may be reused in case of fracture or failure of the leads and extensions of the AIMD. Having the conductive multi-layer polymer catheter tube 400 already implanted within the body would make replacement of leads and extensions considerably easier. This aspect of the disclosed conductive multi-layer polymer catheter tubes becomes particularly advantageous when tunneling through delicate structures such as the neck.

Further, in some examples the conductive multi-layer polymer catheter or the conductive multi-layer polymer catheter tube may surround lengthwise a majority of the insulating jacket. Also, the outer conductive polymer layer of the conductive multi-layer polymer catheter or the conductive multi-layer polymer catheter tube may be in electrical contact with body tissue for optimized dissipation of absorbed electromagnetic energy. The conductive multi-layer polymer catheter and the conductive multi-layer polymer catheter tube thereby substantially reduce electromagnetic coupling to the conductive filer and the AIMD generally.

Figure 5:
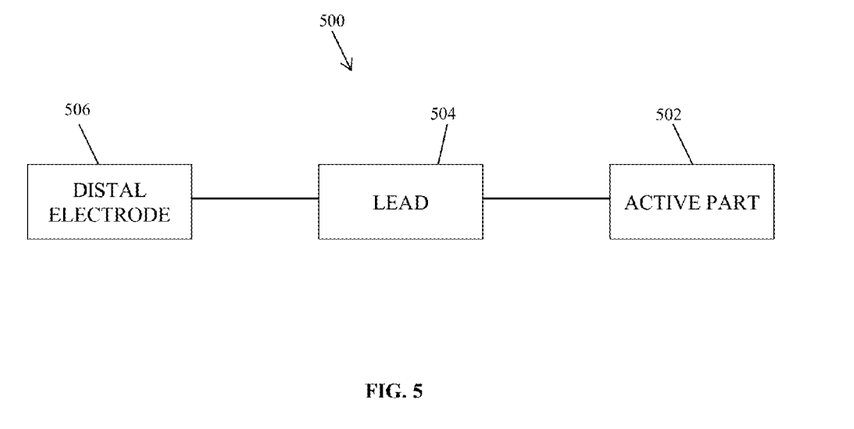
FIG. 5 is a block diagram of an example active implantable medical device.

FIG. 5 is a block diagram of an example AIMD 500. The system includes an active part 502, a lead 504, and a distal electrode 506. The lead 504 has at least one conductive filer electrically coupled to the distal electrode 506.

Although certain example apparatus have been disclosed herein, the scope of coverage of this patent is not limited thereto. To the contrary, this patent covers all methods, apparatus, and articles of manufacture fairly falling within the scope of the appended claims either literally or under the doctrine of equivalents.

What is claimed is:

1. A conductive multi-layer polymer catheter, comprising:
   a lead having at least one conductive filer electrically coupled to a distal electrode and surrounded by at least one insulating jacket,
   an outer conductive polymer layer positioned outside the at least one insulating jacket and configured to contact a body tissue of a patient once implanted;
   an inner conductive polymer layer that can be positioned around and outside the at least one insulating jacket surrounding the at least one conductive filer electrically coupled to the distal electrode; and
   an insulating polymer layer positioned around and outside the inner conductive polymer layer, the insulating polymer layer being positioned within the outer conductive polymer layer, wherein the inner conductive polymer layer, the insulating polymer layer, and the outer conductive polymer layer cooperate to distribute electromagnetic radiation from external sources along at least a portion of a length of the lead of the active implantable medical device, wherein the inner conductive polymer layer, the insulating polymer layer, and the outer conductive polymer layer are slotted lengthwise such that the conductive multi-layer polymer catheter is retrofittable in-situ to a lead of an active implantable medical device or its extension.

* * * * *